(12) United States Patent
Yatabe

(10) Patent No.: US 10,556,041 B2
(45) Date of Patent: Feb. 11, 2020

(54) COATING AGENT AND MEDICAL INSTRUMENT SURFACE TREATED WITH COATING AGENT

(71) Applicant: TERUMO KABUSHIKI KAISHA, Shibuya-ku, Tokyo (JP)

(72) Inventor: Teruyuki Yatabe, Kanagawa (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 70 days.

(21) Appl. No.: 15/855,331

(22) Filed: Dec. 27, 2017

(65) Prior Publication Data
US 2018/0117221 A1 May 3, 2018

Related U.S. Application Data

(63) Continuation of application No. PCT/JP2016/067589, filed on Jun. 13, 2016.

(30) Foreign Application Priority Data

Jul. 1, 2015 (JP) .................................. 2015-132850

(51) Int. Cl.
| | | |
|---|---|---|
| A61B 17/06 | (2006.01) |
| A61L 31/10 | (2006.01) |
| C09D 183/06 | (2006.01) |
| A61M 5/32 | (2006.01) |
| C09D 183/08 | (2006.01) |

(52) U.S. Cl.
CPC .............. *A61L 31/10* (2013.01); *A61M 5/329* (2013.01); *C09D 183/06* (2013.01); *C09D 183/08* (2013.01); *A61B 17/06066* (2013.01); *A61L 2420/02* (2013.01); *A61L 2420/06* (2013.01); *A61M 2205/0222* (2013.01); *A61M 2207/00* (2013.01)

(58) Field of Classification Search
CPC .. A61B 17/06066; C09D 183/08; C08L 83/08
See application file for complete search history.

(56) References Cited

U.S. PATENT DOCUMENTS

| | | | | |
|---|---|---|---|---|
| 3,542,574 A | * | 11/1970 | Payne ....................... | A21D 8/08 106/287.1 |
| 3,814,710 A | * | 6/1974 | Duncan ................... | C08L 83/04 106/10 |
| 4,600,436 A | * | 7/1986 | Traver ..................... | C09G 1/16 106/3 |
| 4,806,430 A | * | 2/1989 | Spielvogel ............ | A61L 29/085 206/571 |

(Continued)

FOREIGN PATENT DOCUMENTS

| | | |
|---|---|---|
| JP | 7-178159 A | 7/1995 |
| JP | 2001-190654 A | 7/2001 |
| JP | 2008-260840 A | 10/2008 |
| JP | 2013-112686 A | 6/2013 |

OTHER PUBLICATIONS

English translation of Written Opinion (PCT/ISA/237) dated Sep. 27, 2016, by the Japanese Patent Office as the International Searching Authority for International Application No. PCT/JP2016/067589.
International Search Report (PCT/ISA/210) dated Sep. 27, 2016, by the Japanese Patent Office as the International Searching Authority for International Application No. PCT/JP2016/067589.
Written Opinion (PCT/ISA/237) dated Sep. 27, 2016, by the Japanese Patent Office as the International Searching Authority for International Application No. PCT/JP2016/067589.

(Continued)

*Primary Examiner* — Margaret G Moore
(74) *Attorney, Agent, or Firm* — Buchanan, Ingersoll & Rooney PC

(57) ABSTRACT

A coating agent that has enhanced durability and a medical instrument (for example, a needle) that has been coated with the coating agent, are provided. The coating agent includes a hydroxyl-group-containing polyorganosiloxane represented by the following general formula (1), a polydiorganosiloxane represented by the following general formula (2), and an amino-group-containing polyorganosiloxane represented by the following general formula (3).

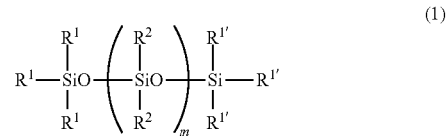

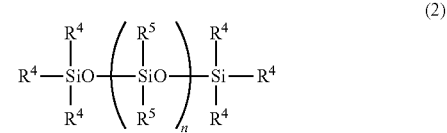

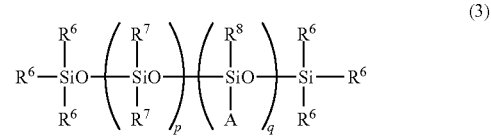

The polydiorganosiloxane (2) is contained in a proportion of a mass ratio to the amino-group-containing polyorganosiloxane (3) of from 0.7:1 to 3.0:1. The hydroxyl-group-containing polyorganosiloxane (1) is contained in a proportion of 2.4 to 5.5 mass %, based on the total mass of the hydroxyl-group-containing polyorganosiloxane (1), the polydiorganosiloxane (2) and the amino-group-containing polyorganosiloxane (3).

19 Claims, 4 Drawing Sheets

(56) References Cited

U.S. PATENT DOCUMENTS

| | | | | |
|---|---|---|---|---|
| 5,536,582 | A * | 7/1996 | Prasad | A61L 31/10 427/387 |
| 6,015,398 | A * | 1/2000 | Arimatsu | A61M 5/32 604/265 |
| 6,936,297 | B2 * | 8/2005 | Roby | A61B 17/06066 427/2.1 |
| 2001/0021832 | A1 * | 9/2001 | Numao | A61L 31/10 604/272 |
| 2003/0114882 | A1 * | 6/2003 | Roby | A61B 17/06066 606/222 |
| 2004/0209784 | A1 * | 10/2004 | Hardman | A61L 29/085 508/204 |
| 2005/0240223 | A1 * | 10/2005 | Roby | A61B 17/06066 606/222 |
| 2011/0152926 | A1 * | 6/2011 | Vetrecin | A61B 17/06 606/223 |
| 2013/0122314 | A1 * | 5/2013 | Ou | A61L 29/085 428/429 |
| 2018/0117220 | A1 * | 5/2018 | Yatabe | A61L 31/00 |
| 2018/0163090 | A1 * | 6/2018 | Ou | C09D 183/14 |

OTHER PUBLICATIONS

Extended European Search Report dated Dec. 7, 2018, issued in EP 16817708.7.

XP 002786666; Database WPI, Week 199537, Thomson Scientific, London, GB; AN 1995-279970.

* cited by examiner

COATING AGENT AND MEDICAL INSTRUMENT SURFACE TREATED WITH COATING AGENT

CROSS-REFERENCES TO RELATED APPLICATIONS

This application is a continuation of International Application No. PCT/JP2016/067589 filed on Jun. 13, 2016, and claims priority to Japanese Application No. 2015-132850 filed on Jul. 1, 2015, the entire content of which is incorporated herein by reference.

TECHNICAL FIELD

The present disclosure generally relates to a coating agent and a medical instrument surface treated with the coating agent.

BACKGROUND DISCUSSION

At present, not only patients suffering from diseases but also healthy persons undergo various medical practices such as medical examinations. For example, injections are used for the patients suffering from diseases, for the purpose of injecting a liquid medicine for therapy, anesthesia at the time of surgery, or the like. In addition, even healthy persons often undergo injections such as blood donation and preventive inoculation. However, injections exert considerable burden on patients and healthy persons, due to a pain at the time of puncture, discomfort at the time of injection of a liquid medicine, or the like. In view of this, for the purpose of alleviating the pain, a variety of investigations have been made on the shape of tip portions of injection needles, coating agents for injection needle surfaces, and the like. Among these, as a coating agent for injection needle surfaces, silicones have been mainly used. The silicone coating agents impart a lubricating property to the injection needle, thereby reducing friction at the time of puncture. Therefore, an injection needle coated with a silicone coating agent alleviates the pain at the time of injection. For example, Japanese Patent Laid-open No. 1995-178159 discloses a silicone coating agent that contains an amino-group-containing polyorganosiloxane and a polydiorganosiloxane in a specific mixing ratio. An injection needle coated with this coating agent exhibits excellent piercing characteristics.

SUMMARY

However, even with the injection needle coated with the coating agent described in Japanese Patent Laid-open No. 1995-178159, it is impossible not to give any pain at all to the subject such as a patient. Accordingly, further enhancement of piercing characteristics can be desirable.

In addition, a needle coated with the silicone coating agent may be used for puncturing multiple times. For example, a needle having been subjected to a silicone coating treatment may be used in injecting a liquid medicine to a patient, after being made to pierce a stopper of a medicine bottle for sucking the liquid medicine. For example, a reservoir needle having been subjected to a silicone coating treatment may be made to re-puncture different infusion bags repeatedly, in the situation of infusion bag replacement. In such cases, there can be a problem that the coating film formed by using the coating agent may peel off the needle surface, increasing the friction (puncture resistance) during use and giving a pain to the patient. For this reason, further enhancement of durability (a restraining or preventing effect on exfoliation of the coating) can be desirable.

Accordingly, aspects of the present disclosure have been made in consideration of the aforesaid circumstances. According to an exemplary aspect, provided is a coating agent enhanced in durability and a medical instrument (for example, a needle) surface treated (coated) with the coating agent.

According to an exemplary aspect, provided is a coating agent enhanced in piercing characteristics and a medical instrument (for example, a needle) surface treated (coated) with the coating agent.

According to an exemplary aspect, for example, it is possible to address the problem by controlling a mixing ratio between an amino-group-containing polyorganosiloxane and a polydiorganosiloxane to within a specified range and, further, using a hydroxyl-group-containing polyorganosiloxane in a specified amount.

According to an exemplary aspect, provided is a coating agent including:

(a) a hydroxyl-group-containing polyorganosiloxane represented by the following general formula (1):

[Chemical 1]

$$R^1-\underset{\underset{R^1}{|}}{\overset{\overset{R^1}{|}}{Si}}O-\left(\underset{\underset{R^2}{|}}{\overset{\overset{R^2}{|}}{Si}}O\right)_m-\underset{\underset{R^{1'}}{|}}{\overset{\overset{R^{1'}}{|}}{Si}}-R^{1'} \qquad (1)$$

where $R^1$ and $R^{1'}$ each independently represent a monovalent hydrocarbon group or a hydroxyl group (—OH), provided that at least one of $R^1$ and at least one of $R^{1'}$ are hydroxyl groups (—OH), $R^2$ each independently represents a monovalent hydrocarbon group, and m is an integer of 1,000 to 30,000;

(b) a polydiorganosiloxane represented by the following general formula (2):

[Chemical 2]

$$R^4-\underset{\underset{R^4}{|}}{\overset{\overset{R^4}{|}}{Si}}O-\left(\underset{\underset{R^5}{|}}{\overset{\overset{R^5}{|}}{Si}}O\right)_n-\underset{\underset{R^4}{|}}{\overset{\overset{R^4}{|}}{Si}}-R^4 \qquad (2)$$

where $R^4$ and $R^5$ each independently represent a monovalent hydrocarbon group, and n is an integer of 8 to 1,000; and (c) an amino-group-containing polyorganosiloxane containing at least one amino group in one molecule thereof represented by the following general formula (3):

[Chemical 3]

$$R^6-\underset{\underset{R^6}{|}}{\overset{\overset{R^6}{|}}{Si}}O-\left(\underset{\underset{R^7}{|}}{\overset{\overset{R^7}{|}}{Si}}O\right)_p-\left(\underset{\underset{A}{|}}{\overset{\overset{R^8}{|}}{Si}}O\right)_q-\underset{\underset{R^6}{|}}{\overset{\overset{R^6}{|}}{Si}}-R^6 \qquad (3)$$

where $R^6$ each independently represents a monovalent hydrocarbon group or a —$OR^9$ group, provided that $R^9$ each independently represents a substituted or unsubstituted $C_1$-$C_4$ monovalent hydrocarbon group, $R^7$ and $R^8$ each independently represent a monovalent hydrocarbon group, A each independently represents an amino-group-containing group, p:q=(5 to 100):1 (that is, a ratio of p:q is in a range of from 5:1 to 100:1), and q is an integer of 1 to 100, in which the polydiorganosiloxane (2) is contained in a proportion of a mass ratio to the amino-group-containing polyorganosiloxane (3) of from 0.7:1 to 3.0:1, and the hydroxyl-group-containing polyorganosiloxane (1) is contained in a proportion of 2.4 to 5.5 mass %, based on the total mass of the hydroxyl-group-containing polyorganosiloxane (1), the polydiorganosiloxane (2), and the amino-group-containing polyorganosiloxane (3).

DETAILED DESCRIPTION

Figure 1A:
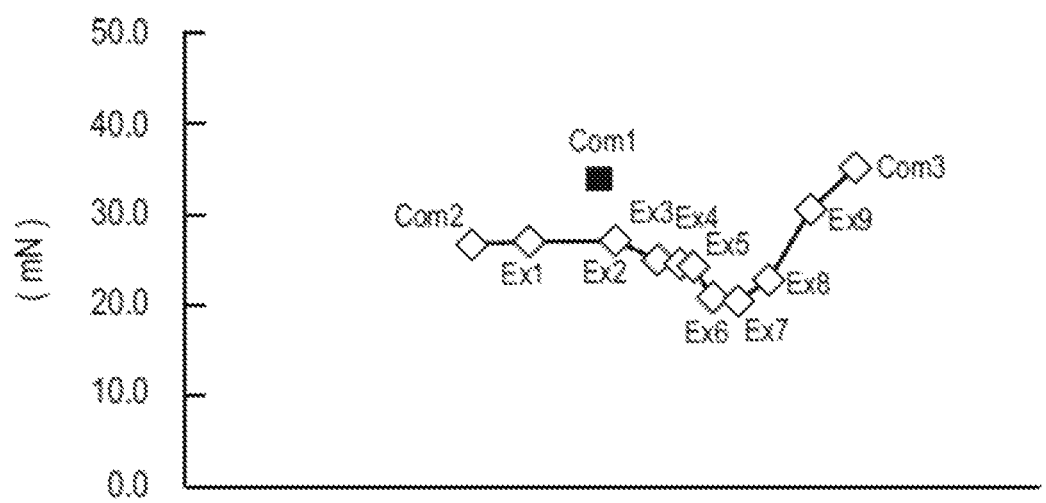
FIG. 1A is a graph depicting puncture resistance (sliding resistance value (mN)) at an initial stage (on puncturing zero time) of a needle surface treated with a coating agent by heating, in Examples 1 to 9 (Ex. 1 to Ex. 9) and Comparative Examples 1 to 3 (Com. 1 to Com. 3).

An exemplary coating agent includes:

(a) a hydroxyl-group-containing polyorganosiloxane represented by the following general formula (1):

[Chemical 4]

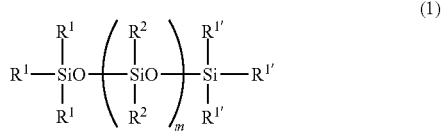

(1)

where $R^1$ and $R^{1'}$ each independently represent a monovalent hydrocarbon group or a hydroxyl group (—OH), provided that at least one of $R^1$ and at least one of $R^{1'}$ are hydroxyl groups (—OH), $R^2$ each independently represents a monovalent hydrocarbon group, and m is an integer of 1,000 to 30,000;

(b) a polydiorganosiloxane represented by the following general formula (2):

[Chemical 5]

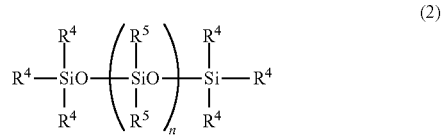

(2)

where $R^4$ and $R^5$ each independently represent a monovalent hydrocarbon group, and n is an integer of 8 to 1,000; and (c) an amino-group-containing polyorganosiloxane containing at least one amino group in one molecule thereof represented by the following general formula (3):

[Chemical 6]

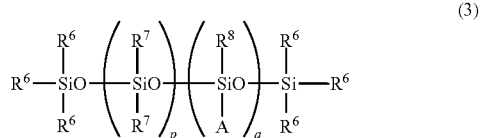

(3)

where $R^6$ each independently represents a monovalent hydrocarbon group or a —$OR^9$ group, provided that $R^9$ each independently represents a substituted or unsubstituted $C_1$-$C_4$ monovalent hydrocarbon group, $R^7$ and $R^8$ each independently represent a monovalent hydrocarbon group, A each independently represents an amino-group-containing group, p:q=(5 to 100):1 (that is, a ratio of p:q is in a range of from 5:1 to 100:1), and q is an integer of 1 to 100, in which the polydiorganosiloxane (2) is contained in a proportion of a mass ratio to the amino-group-containing polyorganosiloxane (3) of from 0.7:1 to 3.0:1, and the hydroxyl-group-containing polyorganosiloxane (1) is contained in a proportion of 2.4 to 5.5 mass %, based on the total mass of the hydroxyl-group-containing polyorganosiloxane (1), the polydiorganosiloxane (2), and the amino-group-containing polyorganosiloxane (3).

For example, an exemplary coating agent having the aforesaid configuration forms a firm coating film, and is excellent in adhesion to a surface of a substrate (for example, a medical instrument such as a needle, a catheter, a cannula, etc.), so that exfoliation of the coating from the substrate can be restrained or prevented and excellent durability can be ensured. In addition, an exemplary coating agent is excellent in lubricating property. Therefore, a needle surface treated with the exemplary coating agent can be reduced in friction (puncture resistance) at the time of puncturing, and can be enhanced in piercing characteristics.

Note that herein the hydroxyl-group-containing polyorganosiloxane represented by the general formula (1) is referred to as the "hydroxyl-group-containing polyorganosiloxane (1)" or the "polyorganosiloxane (1)," the polydiorganosiloxane represented by the general formula (2) is referred to as the "polydiorganosiloxane (2)" or the "polyorganosiloxane (2)," and the amino-group-containing polyorganosiloxane containing at least one amino group in one molecule thereof represented by the general formula (3) is referred to as the "amino-group-containing polyorganosiloxane (3)" or the "polyorganosiloxane (3)."

According to an exemplary embodiment, in the coating agent:

(a) the mass ratio of the polyorganosiloxane (2) to the amino-group-containing polyorganosiloxane (3) is from 0.7:1 to 3.0:1; and (b) the content of the hydroxyl-group-containing polyorganosiloxane (1) is 2.4 to 5.5 mass %, based on the total mass of the polyorganosiloxanes (1) to (3). For example, a coating agent having such a composition is excellent in coating film-forming property, and is excellent in adhesion to a surface of a substrate (for example, a needle, a catheter, a cannula, a three-way cock), and, therefore, exfoliation of a surface treatment product (coating film) obtained by the coating agent from the substrate can be restrained or prevented, and excellent durability can be ensured. In addition, for example, an exemplary coating agent can reduce friction with a substrate, and is excellent in piercing characteristics. Note that the present disclosure is not limited by the following discussion concerning the reason why the aforesaid exemplary effects can be achieved.

Without being bound by any particular theory, extensive and intensive investigations on further enhancement of durability in relation to a substrate and piercing characteristics of coating agents were conducted. For example, according to an exemplary aspect, for enhancing the durability, it can be effective to enhance the strength of a coating film (coating film-forming property) obtained by the coating agent. For example, enhancement of the strength of the coating film (coating film-forming property) was investigated. For example, according to an exemplary aspect, the aforesaid characteristics (a) and (b) can be effective means. For example, the hydroxyl-group-containing polyorganosiloxane (1) has hydroxyl groups at both terminals thereof, which bind to a substrate (for example, hydroxyl groups at a surface of a metallic substrate) and can form comparatively long crosslinked structures, thereby forming a coating film. Therefore, for example, the hydroxyl-group-containing polyorganosiloxane (1) contributes to adhesion to substrate and coating film-forming property. In addition, for example, the polydiorganosiloxane (2), by its organosiloxane moiety, can impart lubricating property to the coating film (enhances piercing characteristics). Further, for example, the amino-group-containing polyorganosiloxane (3) has its polyorganosiloxane moiety contributing to lubricating property (enhancing piercing characteristics) and has its amino group binding to a substrate (for example, hydroxyl groups at a surface of a metallic substrate) (forming comparatively short crosslinked structures), thereby forming the coating film.

Therefore, for example, the amino-group-containing polyorganosiloxane (3) contributes to lubricating property, to adhesion to substrate, and partly to coating film-forming property. For example, the amino-group-containing polyorganosiloxane (3) also contributes to coating film-forming property, to some extent. In an exemplary embodiment, the constituent portions having the amino group for binding to the substrate are not present at both terminals but are present densely in an inner part, and, for this reason, the polyorganosiloxane (3) is higher in strength of coating film, but the hydroxyl-group-containing polyorganosiloxane (1) is higher in coating film forming property. Therefore, for example, with the hydroxyl-group-containing polyorganosiloxane (1) contained in a specified amount, as according to the aforesaid characteristic (b), it is possible to enhance the coating film-forming property obtained using an exemplary coating agent. In addition, for example, with the polyorganosiloxane (3) (which contributes to coating film-forming property) contained in a specified proportion, as according to the aforesaid characteristic (a), it is possible to enhance the strength of the coating film obtained using an exemplary coating agent. For example, due to the firmness of the coating film obtained using the hydroxyl-group-containing polyorganosiloxane (1) and the coating film obtained using the polyorganosiloxane (3), the polydiorganosiloxane (2) is firmly held in the coating film, whereby exfoliation of the polydiorganosiloxane (2) due to friction can be restrained or prevented, and durability can be enhanced. For example, since the hydroxyl groups in the polyorganosiloxane (1) interact with a substrate surface, particularly with hydroxyl groups present at the substrate surface, excellent adhesion to substrate can be ensured. Therefore, for example, a medical instrument (for example, a needle, a catheter, a cannula, a three-way cock) surface treated with an exemplary coating agent can restrain or prevent exfoliation of the surface treatment product (coating film) obtained using the coating agent from the substrate, and can maintain a lubricating property for a long time (is excellent in durability). For example, an exemplary coating agent can reduce friction with a substrate, and is excellent in piercing characteristics. Therefore, for example, when a needle surface treated with an exemplary coating agent is used, exfoliation of the coating film (coating agent) from the needle surface is prevented or restrained, even in the case where the needle is used a plurality of times. For this reason, for example, a high lubricating property can be maintained, and, accordingly, it is possible to reduce friction (puncture resistance) during use and, therefore, to effectively reduce a pain given to the patient. Furthermore, when an exemplary coating agent is used, exfoliation of the coating film from a needle (substrate) surface can be restrained or prevented. Therefore, for example, even where a needle surface treated with an exemplary coating agent is made to re-puncture an infusion bag, mixing of foreign matter (peeled matter of coating film) into the infusion bag is restrained or prevented, which can be desirable from the viewpoint of safety. Note that in Preparation Example 1 (paragraph [0015]) of Japanese Patent Laid-open No. 1995-178159, a both terminal silanol group-containing polydimethylsiloxane is used as a raw material for preparing an amino-group-containing polyorganosiloxane (3). However, this both terminal silanol group-containing polydimethylsiloxane almost entirely reacts with γ-[N-(β-aminoethyl)amino]propylmethyldimethoxysilane, and, therefore, the coating agent of Japanese Patent Laid-open No. 1995-178159 substantially does not contain the polyorganosiloxane (1) (the content is less than 2.4 mass %).

According to an exemplary aspect, the coating agent imparts lubricating property, by the organosiloxane portions of the polydiorganosiloxane (2) and, further, of the amino-group-containing polyorganosiloxane (3). In addition, for example, the amino-group-containing polyorganosiloxane (3) adheres to a substrate through its amino group portions. Therefore, for example, with the polydiorganosiloxane (2) and the amino-group-containing polyorganosiloxane (3) made to be present in a specified proportion, as according to the aforesaid characteristic (a), it is possible to enhance lubricating property of the coating film and reduce friction (puncture resistance) with the substrate, while maintaining adhesion to the substrate. For this reason, for example, when a needle surface treated with an exemplary coating agent is used, the pain given to the patient by the puncture can be further alleviated.

Accordingly, when an exemplary coating agent is applied to a substrate, durability and lubricating property (piercing characteristics) can be enhanced. In addition, for example, when the coating agent is applied to a substrate, a good balance of lubricating property, adhesion and coating film-forming property can be achieved. Therefore, for example, the coating agent can be particularly suitably used for medical instruments where it is desirable to have the aforesaid characteristics, for example, needles such as injection needles. According to an exemplary aspect, provided is a medical instrument (for example, a medical instrument on which friction is generated at the time of insertion into a living body, such as a needle, a catheter, or a cannula) surface treated with a coating agent. Such a medical instrument can ensure that exfoliation of the coating film (coating agent) from the medical instrument surface is prevented or restrained even in the case where the medical instrument is used multiple times. For this reason, a high lubricating property can be maintained, and therefore friction (puncture resistance) during use can be reduced, so that the pain given to the patient can be alleviated effectively. Furthermore, the use of an exemplary coating agent makes it possible to restrain or prevent the coating film from peeling off the medical instrument (substrate) surface. Therefore, even when a needle surface treated with an exemplary coating agent is made to re-puncture an infusion bag, mixing of foreign matter (peeled matter of coating film) into the infusion bag is restrained or prevented, which can be desirable from the viewpoint of safety. In addition, for example, while a three-way cock is not inserted into a living body, a sliding property of an operating part of the three-way cock can be maintained.

Exemplary embodiments will be described below. Herein, "X to Y" indicating a range includes X and Y, and means "not less than X and not more than Y." In addition, unless specified otherwise, operations and measurement of physical properties and the like are conducted under the conditions of room temperature (20° C. to 25° C.) and a relative humidity of 40 to 50% RH.

Note that while an exemplary embodiment in which the medical instrument is a needle will be described in detail below, the present disclosure is not limited to this specific embodiment. For example, the present disclosure is similarly applicable to other medical instruments such as a catheter.

[Hydroxyl-group-containing polyorganosiloxane (1)]

The hydroxyl-group-containing polyorganosiloxane (1) according to an exemplary embodiment is represented by the following general formula (1). Note that in the case where a plurality of constituent units of the formula: —Si(R²)₂O— are present, the constituent units may be identical or different. In addition, an exemplary coating agent may contain a single kind of hydroxyl-group-containing polyorganosiloxane (1) or may contain two or more kinds of hydroxyl-group-containing polyorganosiloxanes (1).

[Chemical 7]

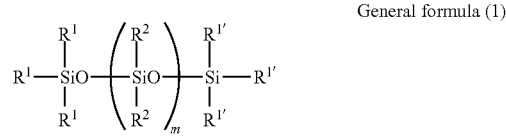

General formula (1)

The hydroxyl-group-containing polyorganosiloxane (1) according to an exemplary embodiment has hydroxyl groups at both terminals thereof, which bind to a substrate (for example, hydroxyl groups at a surface of a metallic substrate) and can form comparatively long crosslinked structures, thereby forming a coating film. Therefore, for example, the coating agent that contains the hydroxyl-group-containing polyorganosiloxane (1) is excellent in coating film-forming property. For this reason, for example, the polydiorganosiloxane (2) and the amino-group-containing polyorganosiloxane (3) can be firmly held in the coating film formed by the hydroxyl-group-containing polyorganosiloxane (1). As a result, for example, when an exemplary coating agent is used, durability can be enhanced. Accordingly, for example, when a needle surface treated with an exemplary coating agent is used, exfoliation of the coating film (coating agent) from the needle surface is prevented or restrained, even in the case where the needle is made to puncture a rubber stopper a plurality of times. For this reason, for example, a needle surface treated with an exemplary coating agent can maintain a high lubricating property, so that friction (puncture resistance) during use is small, and the pain given to the patient can be reduced effectively. For example, even when a needle surface treated with an exemplary coating agent is made to re-puncture an infusion bag, peeling of the coating film (coating agent) from the needle surface and resultant mixing of foreign matter (peeled matter of coating film) into the infusion bag is restrained or prevented, which can be desirable from the viewpoint of safety. In addition, the hydroxyl-group-containing polyorganosiloxane (1) according to an exemplary aspect has hydroxyl groups ($R^1$ and $R^{1'}$) at both terminals. For example the hydroxyl groups interact with a substrate, for example, with hydroxyl groups of the substrate, and, therefore are excellent in adhesion to the substrate. For this reason, for example, the hydroxyl groups promote adhesion to the substrate, together with the amino groups present in the amino-group-containing polyorganosiloxane (3).

For example, the content of the hydroxyl-group-containing polyorganosiloxane (1) is 2.4 to 5.5 mass %, based on the total mass of the hydroxyl-group-containing polyorganosiloxane (1), the polydiorganosiloxane (2) and the amino-group-containing polyorganosiloxane (3). For example, if the content of the polyorganosiloxane (1) is less than 2.4 mass %, the coating film-forming property is low, the polydiorganosiloxane (2) and the amino-group-containing polyorganosiloxane (3) cannot be maintained sufficiently, and lubricating property and durability are poor (Comparative Example 3 below). In contrast, for example, if the content of the polyorganosiloxane (1) exceeds 5.5 mass %, the contents of the polydiorganosiloxane (2) and the amino-group-containing polyorganosiloxane (3) which contribute to imparting of lubricating property are low, so that lubricating property and durability are poor (Comparative Example 2 below). For example, from the viewpoint of further enhancing the coating film-forming property (hence, durability), the content of the hydroxyl-group-containing polyorganosiloxane (1) can be 2.9 to 5.5 mass %, for example, 3.2 to 5.5 mass %, for example, 3.2 to 4.6 mass %, for example, 3.2 to 3.9 mass %, based on the total mass of the hydroxyl-group-containing polyorganosiloxane (1), the polydiorganosiloxane (2) and the amino-group-containing polyorganosiloxane (3). Note that in the case where two or more kinds of hydroxyl-group-containing polyorganosiloxanes (1) are contained, the aforesaid content means the total amount of the hydroxyl-group-containing polyorganosiloxanes (1).

In the aforesaid general formula (1), for example, $R^1$ and $R^{1'}$ represent a monovalent hydrocarbon group or a hydroxyl group (—OH). For example, $R^1$ and $R^{1'}$ may be identical or different. For example, in —Si$(R^1)_3$, the plurality of $R^1$ groups may be identical or different. Similarly, for example, in —Si$(R^{1'})_3$, the plurality of $R^{1'}$ groups may be identical or different. It is to be noted, however, that at least one of $R^1$ groups and at least one of $R^{1'}$ groups are hydroxyl groups (—OH). For example, taking into account a further enhancing effect on coating film-forming property and the like factors, it is exemplary that one or two of $R^1$ groups and/or one or two of $R^{1'}$ groups are hydroxyl groups, and it is exemplary that one of $R^1$ groups and one of $R^{1'}$ groups are hydroxyl groups.

For example, the monovalent hydrocarbon groups as $R^1$ and $R^{1'}$ are not particularly limited, and example thereof include $C_1$-$C_{24}$ straight-chain or branched alkyl groups, $C_2$-$C_{24}$ straight-chain or branched alkenyl groups, $C_3$-$C_9$ cycloalkyl groups, and $C_6$-$C_{30}$ aryl groups. For example, the $C_1$-$C_{24}$ straight-chain or branched alkyl groups are not specifically restricted, and examples thereof include methyl, ethyl, n-propyl, isopropyl, n-butyl, isobutyl, sec-butyl, tert-butyl, n-pentyl, isopentyl, tert-pentyl, neopentyl, 1,2-dimethylpropyl, n-hexyl, isohexyl, 1,3-dimethylbutyl, 1-isopropylpropyl, 1,2-dimethylbutyl, n-heptyl, 1,4-dimethylpentyl, 3-ethylpentyl, 2-methyl-1-isopropylpropyl, 1-ethyl-3-methylbutyl, n-octyl, 2-ethylhexyl, 3-methyl-1-isopropylbutyl, 2-methyl-1-isopropyl, 1-t-butyl-2-methylpropyl, n-nonyl, 3,5,5-trimethylhexyl, n-decyl, isodecyl, n-undecyl, 1-methyldecyl, n-dodecyl, n-tridecyl, n-tetradecyl, n-pentadecyl, n-hexadecyl, n-heptadecyl, n-octadecyl, n-nonadecyl, n-eicosyl, n-heneicosyl, n-docosyl, n-tricosyl, and n-tetracosyl. The $C_2$-$C_{24}$ straight-chain or branched alkenyl groups are not particularly limited, and examples thereof include vinyl, 1-propenyl, 2-propenyl (allyl), isopropenyl, 1-butenyl, 2-butenyl, 3-butenyl, 1-pentenyl, 2-pentenyl, 3-pentenyl, 1-hexenyl, 2-hexenyl, 3-hexenyl, 1-heptenyl, 2-heptenyl, 5-heptenyl, 1-octenyl, 3-octenyl, 5-octenyl, dodecenyl, and octadecenyl. The $C_3$-$C_9$ cycloalkyl groups are not specifically restricted, and examples thereof include cyclopropyl, cyclobutyl, cyclopentyl, cyclohexyl, cycloheptyl, and cyclooctyl. The $C_6$-$C_{30}$ aryl groups are not particularly limited, and examples thereof include phenyl, biphenyl, terphenyl, pentalenyl, indenyl, naphthyl, azulenyl, heptalenyl, biphenylenyl, fluorenyl, acenaphthylenyl, pleiadenyl, acenaphthenyl, phenalenyl, phenanthryl, anthryl, fluoranthenyl, acephenanthrylenyl, aceanthrylenyl, triphenylenyl, pyrenyl, crysenyl, and naphthacenyl. Among these, from the viewpoint of a further enhancing effect on lubricating property, compatibility with solvents, and the like factors, $R^1$ and $R^{1'}$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, methyl groups. Note that the "compatibility" refers to mutual solubility between different kinds of molecules, and means ease of mixing at a molecular level.

In the aforesaid general formula (1), for example, $R^2$ represents a monovalent hydrocarbon group. For example, the $R^2$ groups present in one constituent unit may be identical or different. In addition, for example, in the case where a plurality of constituent units are present, the constituent units may be identical or different. The monovalent hydrocarbon group as $R^2$ can be selected from the examples set forth for the aforesaid $R^1$ and $R^{1'}$, and, therefore, description thereof is omitted here. For example, from the viewpoint of a further enhancing effect on lubricating property and durability, compatibility with solvents, and the like factors, $R^2$ can be a $C_1$-$C_{16}$ straight-chain or branched alkyl group, for example, a $C_1$-$C_8$ straight-chain or branched alkyl group, for example, a $C_1$-$C_4$ straight-chain or branched alkyl group, for example, a methyl group.

For example, according to an exemplary embodiment, in the general formula (1), one of $R^1$ and $R^{1'}$ is a hydroxyl group, the rest of the $R^1$ and $R^{1'}$ are each independently a $C_1$-$C_4$ straight-chain or branched alkyl group, and $R^2$ is each independently a $C_1$-$C_4$ straight-chain or branched alkyl group. In addition, according to an exemplary embodiment, in the general formula (1), one of $R^1$ and $R^{1'}$ is a hydroxyl group, the rest of the R1 and R1' are methyl groups, and $R^2$ is a methyl group.

For example, m is an integer of 1,000 to 30,000, for example, an integer of 5,000 to 20,000, for example, 10,000 to 15,000. When m is in the aforesaid range, the polyorganosiloxane (1) can exhibit a sufficient coating film formation. While the molecular weight of the hydroxyl-group-containing polyorganosiloxane (1) is not particularly limited, it is exemplary that the weight average molecular weight is 10,000 to 2,000,000, for example, 100,000 to 1,050,000, for example, 100,000 to 1,000,000, for example, 500,000 to 1,000,000. Herein the weight average molecular weight means a value determined by a calibration curve method from measurement results obtained by gel permeation chromatography (GPC) with polystyrene as a standard substance.

[Polydiorganosiloxane (2)]

The polydiorganosiloxane (2) according to an exemplary aspect is represented by the following general formula (2):

[Chemical 8]

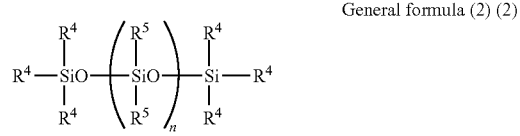

General formula (2) (2)

As indicated by the aforesaid structure, for example, the polydiorganosiloxane (2) is a polydiorganosiloxane which has a triorganosilyl group at molecular chain terminals and does not contain an amino group in its molecule, and substantially contains no hydroxyl group and no hydrolysable group in its molecule.

For example, the polydiorganosiloxane (2), by its organosiloxane moiety, imparts a lubricating property to a coating film formed by the hydroxyl-group-containing polyorganosiloxane (1) and the amino-group-containing polyorganosiloxane (3). Due to the presence of the polydiorganosiloxane (2), for example, the coating film formed can exhibit a high lubricating property (ease of piercing, or piercing resistance-reducing effect). For example, in the case where a plurality of constituent units represented by the formula: —Si($R^5$)$_2$O— are present, the constituent units may be identical or different. Further, for example, an exemplary coating agent may contain a single kind of polydiorganosiloxane (2), or may contain two or more kinds of polydiorganosiloxanes (2).

An exemplary coating agent contains the polydiorganosiloxane (2) in such an amount that its proportion in terms of mass ratio to the amino-group-containing polyorganosiloxane (3) is from 0.7:1 to 3.0:1. For example, if the mass ratio of the polydiorganosiloxane (2) to the polyorganosiloxane (3) is less than 0.7, the proportion of the polydiorganosiloxane (2) is too low, and a sufficient lubricating property cannot be imparted. In contrast, for example, if the mass ratio of the polydiorganosiloxane (2) to the polyorganosiloxane (3) exceeds 3.0, the proportion of the polyorganosiloxane (3) is too low, and adhesion property is poor, so that sufficient durability cannot be imparted. Taking into account a further enhancing effect on lubricating property and durability and the like factors, for example, the mass ratio of the polydiorganosiloxane (2) to the amino-group-containing polyorganosiloxane (3) can be from 0.9 to 2.5, for example, from 1.1 to 2.4, for example, 1.1 to 2.0, for example, from 1.5 to 2.0.

For example, the content of the polydiorganosiloxane (2) is not particularly limited so long as the aforesaid mass ratio to the amino-group-containing polyorganosiloxane (3) is satisfied. Taking into account a better balance of lubricating property, adhesion and coating film-forming property, the content of the polydiorganosiloxane (2) can be 40 to 75 mass %, for example, 40 to 70 mass %, for example, 40 to 65 mass %, for example, 50 to 65 mass %, for example, 58 to 65 mass %, based on the total mass of the hydroxyl-group-containing polyorganosiloxane (1), the polydiorganosiloxane (2) and the amino-group-containing polyorganosiloxane (3). When the content of the polydiorganosiloxane (2) is such an amount, for example, lubricating property (ease of piercing, or a piercing resistance-reducing effect) and durability can be enhanced more effectively. Note that in the case where two or more kinds of polydiorganosiloxanes (2) are contained, the aforesaid content means the total amount of the polydiorganosiloxanes (2).

For example, in the aforesaid general formula (2), $R^4$ and $R^5$ represent monovalent hydrocarbon groups. For example, the plurality of $R^4$ groups may be identical or different. Similarly, the plurality of $R^5$ groups may be identical or different. The monovalent hydrocarbon groups as $R^4$ and $R^5$ can be selected from the examples set forth for the aforesaid general formula (1), and, therefore, description thereof is omitted here. Among these, for example, the monovalent hydrocarbon groups as $R^4$ and $R^5$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, methyl groups, from the viewpoint of a further enhancing effect on lubricating property and the like factors.

For example, according to an exemplary embodiment, in the general formula (2), $R^4$ and $R^5$ are each independently a $C_1$-$C_4$ straight-chain or branched alkyl group. In addition, according to an exemplary embodiment, in the general formula (2), $R^4$ and $R^5$ are methyl groups.

In the aforesaid general formula (2), for example, n is an integer of 8 to 1,000, for example, an integer of 10 to 200, for example, an integer of 20 to 100, for example, an integer of 30 to 50. With such n as aforesaid, for example, the polydiorganosiloxane (2) exhibits a sufficient lubricating property, whereby friction with a substrate (puncture resistance) can be further reduced. Therefore, for example, while the molecular weight of the polydiorganosiloxane (2) is not particularly limited, it is exemplary that the weight average molecular weight is 500 to 7,000, for example, 1,500 to 5,000, for example, 2,000 to 4,000.

Examples of the polydiorganosiloxane (2) include polydimethylsiloxane, polydiethylsiloxane, polydipropylsiloxane, polydiisopropylsiloxane, polymethylethylsiloxane, polymethylpropylsiloxane, polymethylisopropylsiloxane, polyethylpropylsiloxane, and polyethylisopropylsiloxane. Among these, exemplary are polydimethylsiloxane and polydiethylsiloxane. Polydimethylsiloxane is exemplary from the viewpoint of lubricating property (piercing characteristics) and the like.

[Amino-group-containing polyorganosiloxane (3)]

The amino-group-containing polyorganosiloxane (3) according to an exemplary aspect is represented by the following general formula (3):

[Chemical 9]

General formula (3) (3)

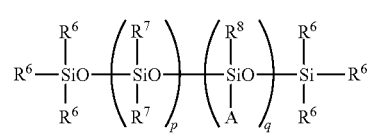

The amino-group-containing polyorganosiloxane (3) according to an exemplary aspect can bind (adhere) to a substrate by interacting with hydroxyl groups present in the substrate, for example, at the substrate surface through the amino group (the substituent group "A" in the general formula (3)). In addition, for example, the organosiloxane moiety (—Si($R^7$)$_2$O—) present in the amino-group-containing polyorganosiloxane (3) according to an exemplary embodiment imparts lubricating property (ease of piercing). In the case where two or more constituent units of the formula: —Si($R^7$)$_2$O— are present (p is not less than two), the constituent units may be identical or different. Similarly, in the case where two or more constituent units of the formula: —Si($R^8$)(A)O— are present (q is not less than 2), the constituent units may be identical or different. Further, for example, the coating agent may contain a single kind of amino-group-containing polyorganosiloxane (3), or may contain two or more kinds of amino-group-containing polyorganosiloxanes (3).

For example, the content of the amino-group-containing polyorganosiloxane (3) is not particularly limited, so long as the aforesaid mass ratio in relation to the polydiorganosiloxane (2) is satisfied. For example, taking into account a better balance of lubricating property, adhesion and coating film-forming property, the content of the amino-group-containing polyorganosiloxane (3) can be 24 to 57 mass %, for example, 28 to 54 mass %, for example, 32 to 54 mass %, for example, 32 to 45 mass %, for example, 32 to 38 mass %, based on the total mass of the hydroxyl-group-containing polyorganosiloxane (1), the polydiorganosiloxane (2) and the amino-group-containing polyorganosiloxane (3). When the content of the amino-group-containing polyorganosiloxane (3) is such an amount, for example, adhesion to a substrate and lubricating property (ease of piercing, or piercing resistance-reducing effect) can be enhanced more effectively. In addition, for example, safety of the coating agent can be further enhanced, which can be desirable in the case of application to medical uses, such as a needle.

For example, in the aforesaid general formula (3), $R^6$ is a monovalent hydrocarbon group or a —$OR^9$ group. For example, the plurality of $R^6$ groups may be identical or different. For example, the monovalent hydrocarbon group can be selected from the examples set forth for the aforesaid general formula (1), and, therefore, description thereof is omitted here. For example, $R^6$ can be $C_1$-$C_{16}$ straight-chain or branched alkyl groups, for example, $C_1$-$C_8$ straight-chain or branched alkyl groups, for example, $C_1$-$C_4$ straight-chain or branched alkyl groups, for example, a methyl group, from the viewpoint of a further enhancing effect on lubricating property and durability, compatibility with solvents, and the like factors.

In addition, for example, $R^9$ each independently represents a substituted or unsubstituted $C_1$-$C_4$ monovalent hydrocarbon group. For example, in the case where the plurality of $R^6$ groups are —$OR^9$ groups, the plurality of —$OR^9$ groups may be identical or different from one another. For example, the monovalent hydrocarbon group is not specifically restricted, and can be, for example, a $C_1$-$C_4$ straight-chain or branched alkyl group (methyl, ethyl, n-propyl, isopropyl, n-butyl, isobutyl, sec-butyl, tert-butyl), a $C_2$-$C_4$ straight-chain or branched alkenyl group (vinyl, 1-propenyl, 2-propenyl (allyl), isopropenyl, 1-butenyl, 2-butenyl, 3-butenyl), or a $C_3$ or $C_4$ cycloalkyl group (cyclopropyl, cyclobutyl). For example, methyl and ethyl groups are exemplary from the viewpoint of a further enhancing effect on lubricating property, adhesion to a substrate, and the like factors.

For example, in the aforesaid general formula (3), $R^7$ and $R^8$ represent a monovalent hydrocarbon group. Each $R^7$ in the organosiloxane moiety (—$Si(R^7)_2O$—) and $R^8$ in the constituent unit of the formula: —$Si(R^8)(A)O$— may be identical or different. For example, the monovalent hydrocarbon group is not specifically restricted, and is defined in the same manner as the aforesaid substituent group "$R^6$," and can be selected from the examples set forth for the aforesaid general formula (1), and, therefore, description thereof is omitted here. Among these, exemplary are $C_1$-$C_4$ straight-chain alkyl groups, for example, a methyl group, from the viewpoint of a further enhancing effect on lubricating property, availability, and the like factors.

In the aforesaid general formula (3), A represents an amino-group-containing group. For example, in the case where a plurality of A groups are present (q is not less than two), the A groups may be identical or different. The amino-group-containing group is not particularly limited, and examples thereof include β-aminoethyl, γ-aminopropyl, N-(β-aminoethyl)aminomethyl, and γ-(N-(β-aminoethyl)amino)propyl. Among these, exemplary is γ-aminopropyl, N-(β-aminoethyl)aminomethyl or γ-(N-(β-aminoethyl)amino)propyl, for example, γ-(N-(β-aminoethyl)amino)propyl or γ-aminopropyl, for example, γ-(N-(β-aminoethyl)amino)propyl, from the viewpoint of a further enhancing effect on lubricating property, adhesion to a substrate, and the like factors.

For example, according to an exemplary embodiment, in the general formula (3), $R^6$ is each independently a $C_1$-$C_4$ straight-chain or branched alkyl group, $R^7$ and $R^8$ are each independently a $C_1$-$C_4$ straight-chain or branched alkyl group, and A is γ-aminopropyl, N-(β-aminoethyl)aminomethyl or γ-(N-(β-aminoethyl)amino)propyl group. According to an exemplary embodiment, in the general formula (3), $R^6$ is methyl, $R^7$ and $R^8$ are methyl, and A is γ-(N-(β-aminoethyl)amino)propyl.

For example, in the aforesaid general formula (3), q is an integer of 1 to 100, for example, an integer of 3 to 20, for example, an integer of 3 to 15, for example, an integer of 4 to 10. For example, p is an integer which together with q satisfies the relation of p:q=(5 to 100):1 (molar ratio) (that is, a ratio of p:q is in a range of from 5:1 to 100:1). For example, p:q=(10 to 100):1, for example, (20 to 80):1, for example, (30 to 50):1. That is, for example, a ratio of p:q is in a range of from 10:1 to 100:1, for example, 20:1 to 80:1, for example, 30:1 to 50:1. With p and q being as aforesaid, for example, a sufficient number of amino groups are present in the amino-group-containing polyorganosiloxane (3), and, therefore, sufficient adhesion to a substrate can be achieved. For example, with such p and q, for example, a sufficient number of organosiloxane moieties are present in the amino-group-containing polyorganosiloxane (3), so that the coating agent can exhibit a sufficient lubricating property, thereby further reducing friction with a substrate (puncture resistance). For example, while p is not particularly limited so long as it satisfies the aforesaid relation, p can be 10 to 800, for example, 60 to 400, for example, 100 to 300.

The molecular weight of the amino-group-containing polyorganosiloxane (3) is not particularly limited, for example, the weight average molecular weight can be 5,000 to 50,000, for example, 7,500 to 30,000, for example, 10,000 to 20,000.

A method of preparing the amino-group-containing polyorganosiloxane (3) according to an exemplary aspect is not specifically restricted. For example, the amino-group-containing polyorganosiloxane (3) according to an exemplary aspect can be prepared in the same manner as, or with appropriate modification of, the method described in, for example, Japanese Patent Laid-open No. 1995-178159.

The coating agent according to an exemplary aspect contains the hydroxyl-group-containing polyorganosiloxane (1), the polydiorganosiloxane (2) and the amino-group-containing polyorganosiloxane (3). For example, the coating agent according to an exemplary aspect may be composed only of the polyorganosiloxanes (1) to (3), or may further contain other ingredients in addition to the aforesaid ingredients. In the latter case, the other ingredients usable are not specifically restricted, and examples thereof include those ingredients that are suitable for being added to coating agents, for example, coating agents for coating of medical instruments (e.g., injection needles, catheters, cannulas). Examples include condensation reaction catalysts, antioxidants, coloring matters, surfactants, slip agents, and priming agents. For example, the content of the other ingredients is not particularly limited so long as the effects of the polyorganosiloxanes (1) to (3) are not spoiled, and can be approximately 0.1 to 5 mass % based on the total amount of the polyorganosiloxanes (1) to (3).

In addition, the coating agent according to an exemplary aspect may contain an organic solvent. For example, the organic solvent is not specifically restricted, and the same or similar solvents to those used in coating agents can be used. Examples of the organic solvent include flon solvents such as 1,1,2-trichloro-1,2,2-trifluoroethane, etc., chlorine-containing hydrocarbons such as methylene chloride (dichloromethane), chloroform, etc., aliphatic hydrocarbons such as butane, pentane, hexane, etc., aromatic hydrocarbons such as benzene, toluene, xylene, etc., esters such as ethyl acetate, butyl acetate, etc., water-insoluble ketones such as methyl isobutyl ketone, etc., ethers such as tetrahydrofuran (THF), butyl ether, dioxane, etc., aliphatic alcohols such as methanol, ethanol, isopropanol, etc., volatile siloxanes such as hexamethyldisiloxane, octamethylcyclotetrasiloxane, etc., acetonitrile, dimethyl formamide (DMF), dimethyl sulfoxide (DMSO), and carbon disulfide. These organic solvents may be used either singly or as a mixed solvent obtained by combining two or more of these solvents. The amount of the organic solvent to be used is not particularly limited. From the viewpoint of ease of coating and the like factors, for example, the amount of the organic solvent can be such that the total concentration of the polyorganosiloxanes (1) to (3) is approximately 5 to 80 mass %, for example, approximately 57 to 77 mass %. Note that in the case where a medical instrument (e.g., a needle) is coated with the coating agent according to an exemplary aspect, the coating agent may further be diluted with the aforesaid organic solvent. In this case, it is exemplary to dilute the coating agent with the organic solvent in such a manner that the total concentration of the polyorganosiloxanes (1) to (3) is 1 to 10 mass %, for example, 3 to 7 mass %.

The method of preparing the coating agent according to an exemplary aspect is not specifically restricted, and there can be used a method in which the hydroxyl-group-containing polyorganosiloxane (1), the polydiorganosiloxane (2) and the amino-group-containing polyorganosiloxane (3), together with the aforesaid other ingredients, if desired, are mixed in the aforesaid composition, and stirring and mixing are conducted. In the aforesaid method, it is exemplary to add an organic solvent. As a result, for example, a medical instrument (e.g., a needle) or the like can be coated with the coating agent. For example, the organic solvent is not particularly limited, and the organic solvents described as the aforesaid other ingredients can be used. For example, stirring and mixing conditions are not specifically restricted. For example, a stirring and mixing temperature can be 25° C. to 130° C., for example, 50° C. to 100° C. In addition, a stirring and mixing time can be 0.5 to 5 hours, for example, 1 to 3 hours. Under such conditions, for example, the hydroxyl-group-containing polyorganosiloxane (1), the polydiorganosiloxane (2) and the amino-group-containing polyorganosiloxane (3), together with the aforesaid other ingredients, if desired, can be uniformly mixed without causing undesirable reactions.

[Use of the Coating Agent]

The aforesaid coating agent according to an exemplary aspect can enhance lubricating property and durability of an object to be coated. Therefore, for example, the coating agent can be suitably used in the field of medical instruments (for example, needles, catheters, cannulas) that highly demand the aforesaid characteristics. According to an exemplary aspect, provided is a medical instrument surface treated by a curing treatment of an exemplary coating agent. In addition, for example, provided is a method of producing a medical instrument that includes subjecting a surface of the medical instrument to a curing treatment with the coating agent according to an exemplary aspect.

For example, the medical instrument may be used in any application where the aforesaid characteristics are desired. Examples of the applicable use include catheters, cannulas, needles, three-way cocks, and guide wires. Among these, an exemplary coating agent can be used for catheters, cannulas, needles and three-way cocks, for example, for needles, for example, medical needles (for example, injection needles). For example, in an exemplary embodiment, there is provided a needle surface treated by a curing treatment of the coating agent according to an exemplary aspect. According to an exemplary coating agent, friction at the time of puncture is reduced, and, for example, durability of the coating is excellent. From the viewpoint of these characteristics, for example, the needle, for example, the medical needle (for example, injection needle), is exemplary as the puncture resistance (maximum resistance value) after puncturing a rubber stopper by the needle ten times is smaller. For example, the aforesaid puncture resistance (maximum resistance value) is less than 45 mN, for example, not more than 41 mN. Note that, for example, as for the lower limit for the puncture resistance (maximum resistance value) after puncturing a rubber stopper by the needle ten times, a lower value is more desirable; therefore, the lower limit is not particularly restricted, and can be 0 mN, and a value of not less than 10 mN is allowable. The puncture resistance (maximum resistance value) can be measured by the method described in Examples.

In addition, for example, provided is a method of producing a needle (medical needle) that includes subjecting a surface of a needle (medical needle) to a curing treatment with the coating agent according to an exemplary aspect.

For example, the medical instrument (as a substrate) may be formed of any material, and the same or similar materials to conventional ones can be used. While the following description will be made by taking as an example an embodiment in which the medical instrument is a needle, the present disclosure is not limited to the following embodiment, and the present disclosure is applicable, for example, by using a material constituting a desired medical instrument in place of a material constituting a needle.

For example, the needle may be formed of any material, and there can be used the same or similar materials to those usually used for needles, for example, medical needles (for example, injection needles), such as metallic materials and polymeric materials. Examples of the metallic materials include, but are not limited to, various stainless steels (SUS) such as SUS304, SUS316L, SUS420J2, SUS630, etc., gold, platinum, silver, copper, nickel, cobalt, titanium, iron, aluminum, tin, various alloys such as nickel-titanium (Ni—Ti) alloys, nickel-cobalt (Ni—Co) alloys, cobalt-chromium (Co—Cr) alloys, zinc-tungsten (Zn—W) alloys, etc., and, further, metal-ceramic composite materials. The aforesaid metallic materials may be used either singly or in combination of two or more of them. The aforesaid metallic materials can ensure that hydroxyl groups on the substrate surface are bound with the amino groups of the amino-group-containing polyorganosiloxane (3) constituting the coating agent and the hydroxyl groups of the hydroxyl-group-containing polyorganosiloxane (1) constituting the coating agent. Therefore, for example, the needles formed of the aforesaid materials are excellent in adhesion to the coating film formed by use of an exemplary coating agent. Examples of the polymeric materials include, but are not limited to, polyamide resins such as nylon 6, nylon 11, nylon 12, nylon 66 (all registered trademarks), etc., polyolefin resins such as polyethylene resins including linear low-density polyethylene (LLDPE), low-density polyethylene (LDPE) and high-density polyethylene (HDPE), and polypropylene resins, etc., modified polyolefin resins, epoxy resins, urethane resins, diallyl phthalate resins (allyl resins), polycarbonate resins, fluoro-resins, amino resins (urea resins, melamine resins, benzoguanamine resins), polyester resins, styrene resins, acrylic resins, polyacetal resins, vinyl acetate resins, phenolic resins, vinyl chloride resins, silicone resins (silicon resins), polyether resins, and polyimide resins. The aforesaid polymeric materials may be used either singly or in combination of two or more of them.

In addition, for example, the substrate to be surface treated with the coating agent according to an exemplary aspect can be a substrate having a functional group such as a hydroxyl group, a carboxyl group and an amino group, from the viewpoint of easy interaction with the functional groups such as amino group and hydroxyl group possessed by an exemplary coating agent. For example, in the case where the substrate is a metallic material, the metallic material is coated on its surface with an oxide film and has hydroxyl groups or the like, so that the metallic material is high in adhesion to an exemplary coating agent. For example, in the case of a substrate having little interaction with the functional groups such as amino group and hydroxyl group possessed by an exemplary coating agent, functional groups such as hydroxyl group may be imparted to the substrate by a plasma treatment or the like, whereby adhesion between the coating agent and the substrate can be enhanced.

While the method for surface treatment with the coating agent according to an exemplary aspect is not specifically restricted, it is exemplary that a curing treatment is conducted by heating, or irradiating with radiation, a coating film that contains the coating agent. For example, provided is a method of producing a medical instrument (for example, a needle), the method including forming a coating film containing an exemplary coating agent on a surface of a medical instrument (for example, a needle) and performing a curing treatment by heating, or irradiating with radiation, the coating film. Alternatively, for example, the surface treatment method by the coating agent according to an exemplary aspect can include performing a curing treatment by heating and humidifying a coating film that contains the coating agent. For example, provided is a method of producing a medical instrument (for example, a needle), the method including forming a coating film containing the coating agent on a surface of a medical instrument (for example, a needle) and performing a curing treatment by heating and humidifying the coating film.

For example, the method of forming the coating film containing the coating agent is not specifically restricted, and any suitable application methods can be applied. For example, as a technique of performing coating, there can be applied an immersion method (dipping method), an applying or printing method, a spraying method, a brushing method, a spin coating method, a coating agent-impregnated sponge coating method and the like. Note that in the case of coating a needle surface with the coating agent, for example, a gas such as air may be fed into the inside of the needle to, for example, thereby prevent the coating agent from entering into the inside of the needle. For example by this, clogging of the needle with the coating agent can be prevented from occurring. In addition, for example, the coating agent with which a substrate is coated may be subjected to volatilization of solvent by natural drying, air-drying, heating or the like, if desired, or may in some cases be subjected to precuring of the coating agent simultaneously.

For example, in the case of forming a coating film on only part of the needle surface, only part of the needle surface may be immersed in the coating agent to coat part of the needle surface with the coating agent (coating solution), thereby forming a coating film on a desired surface part of the needle surface. For example, in the case where it is difficult to immerse only part of the needle surface in the coating agent, a process may be adopted in which a needle surface part not needing formation of a coating film thereon is preliminarily protected (e.g., covered) with an appropriate member or material that is attachable and detachable, then the needle is immersed in the coating agent to coat the needle surface with the coating agent, and the protective member (material) on the needle surface part not needing the formation of a coating film is detached, whereby a coating film can be formed on only a desired surface part of the needle surface. It is to be noted, however, that the present disclosure is not limited in any way to these formation methods, and a coating film can be formed by appropriately utilizing any suitable methods. For example, in the case where it is difficult to immerse only part of a needle surface in the coating agent, other coating method (for example, application method, spraying method, etc.) than the immersion method may be applied in place of the immersion method. For example, in the case where both the outer surface and the inner surface of the needle surface are to have a lubricating property and durability, an immersion method (dipping method) can be used, in view of that both the outer surface and the inner surface can thereby be coated at a time.

For example, after the coating film containing the coating agent is formed as aforesaid, a curing treatment of the coating film can be conducted. In regard of the aforesaid curing treatment (surface treatment), the method for the curing treatment (surface treatment) in the case of heating the coating film containing the coating agent is not specifically restricted. Examples of the curing treatment (surface treatment) include a heating treatment under normal pressure (atmospheric pressure), a heating treatment under compressed steam, and a heating treatment using ethylene oxide gas (EOG).

For example, heating treatment conditions (reaction conditions) in the case of the heating treatment under normal pressure (atmospheric pressure) are not particularly limited, so long as they are conditions under which a desired effect (for example, lubricating property, durability) can be achieved. The heating temperature can be 50° C. to 150° C., for example, 60° C. to 130° C. In addition, the heating time can be 2 to 48 hours, for example, 15 to 30 hours. For example, under such reaction conditions, the amino-group-containing polyorganosiloxane (3) (amino group) and the hydroxyl-group-containing polyorganosiloxane (1) (hydroxyl group) can firmly bind to a substrate. For example, the hydroxyl-group-containing polyorganosiloxane (1) (hydroxyl group) reacts with the substrate surface, whereby a firm coating film can be formed. In addition, for example, as the heating means (device), there can be utilized, for example, an oven, a dryer, a microwave heater and the like.

For example, heating treatment conditions (reaction conditions) in the case of the heating treatment under compressed steam are also not particularly limited, so long as they are conditions under which a desired effect (for example, lubricating property, durability) can be achieved. The hearing temperature can be 100° C. to 135° C., for example, 105° C. to 130° C. In addition, the heating time can be 1 to 120 minutes, for example, 10 to 60 minutes. Further, the pressure may be appropriately selected, taking a desired reactivity (for example, lubricating property, durability, binding property for binding to a substrate) and the like into consideration. Under such reaction conditions, for example, the amino-group-containing polyorganosiloxane (3) (amino group) and the hydroxyl-group-containing polyorganosiloxane (1) (hydroxyl group) can firmly bind to a substrate. For example, the hydroxyl-group-containing polyorganosiloxane (1) (hydroxyl group) reacts with the substrate surface, whereby a firm coating film can be formed. In addition, for example, under the aforesaid conditions, a needle can be simultaneously subjected to a sterilization treatment. For example, as the heating means (device), there can be utilized, for example, a Koch's sterilizer, an autoclave and the like.

For example, heating treatment conditions (reaction conditions) in the case of the heating treatment using ethylene oxide gas (EOG) are also not particularly limited, so long as they are conditions under which a desired effect (for example, lubricating property, durability) can be achieved. The heating temperature can be 40° C. to 135° C., for example, 45° C. to 80° C. In addition, the heating time can be 1 to 300 minutes, for example, 20 to 250 minutes. Further, the pressure may be appropriately selected, taking a desired reactivity (for example, lubricating property, durability, binding property for binding to a substrate) and the like into consideration. Under such reaction conditions, for example, the amino-group-containing polyorganosiloxane (3) (amino group) and the hydroxyl-group-containing polyorganosiloxane (1) (hydroxyl group) can firmly bind to a substrate. For example, the hydroxyl-group-containing polyorganosiloxane (1) (hydroxyl group) reacts with the substrate surface, whereby a firm coating film can be formed. In addition, for example, under the aforesaid conditions, a needle can simultaneously be subjected to a sterilization treatment.

For example, the radiation in the case of performing the aforesaid surface treatment (curing treatment) by irradiation with radiation is not specifically restricted, and can be gamma rays (γ rays), electron beams, neutron beams, or X rays. Among these, exemplary are gamma rays and electron beams. By irradiating with radiation, for example, it is possible not only to accelerate the curing treatment of the coating agent but also to sterilize the needle. Radiation irradiation conditions (reaction conditions) are not specifically restricted, so long as they are conditions under which a desired effect (for example, lubricating property, durability) can be achieved. For example, in the case of irradiation with gamma rays, the conditions such as dose and irradiation time are not particularly limited. For example, γ ray dose can be 10 to 50 kGy, for example, 15 to 25 kGy. Under such irradiation conditions, the amino-group-containing polyorganosiloxane (3) (amino group) and the hydroxyl-group-containing polyorganosiloxane (1) (hydroxyl group) can firmly bind to a substrate. In addition, for example, the hydroxyl-group-containing polyorganosiloxane (1) (hydroxyl group) reacts with the substrate surface, whereby a firm coating film can be formed.

EXAMPLES

Exemplary effects of the present disclosure will be described below, using the following Examples and Comparative Examples. It is to be noted, however, that the technical scope of the present invention is not to be limited to the following Examples. Note that in the following Examples, the operations were carried out at room temperature (25° C.), unless specified otherwise. In addition, "%" and "parts" mean "mass %" and "parts by mass," respectively, unless otherwise specified.

Synthesis Example 1

Synthesis of Both Terminal Amino Group-Containing Polyorganosiloxane (4)

A both terminal amino group-containing polyorganosiloxane (4) of the following structure was synthesized in the same manner as in Preparation Example 1 of Japanese Patent Laid-open No. 1995-178159, in the following way.

Both terminal amino group-containing polyorganosiloxane (4)

[Chemical 10]

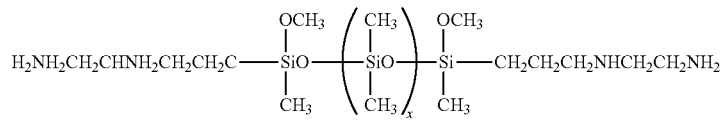

In the aforesaid structure, x=12,000

390 parts of toluene was added to 100 parts by mass of a both terminal silanol group-containing polydimethylsiloxane (weight average molecular weight=approximately 900,000) of the following structure, the resulting admixture was stirred for three hours at 50° C., then 20 parts by mass of γ-[N-(β-aminoethyl)amino]propylmethyldimethoxysilane was added thereto, and reaction was allowed at 80° C. for 12 hours, to obtain the both terminal amino group-containing polyorganosiloxane (4) (weight average molecular weight=approximately 900,000).

Both terminal silanol group-containing polydimethylsiloxane

[Chemical 11]

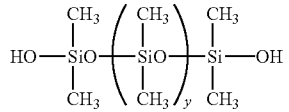

Comparative Example 1

120 parts by mass of the both terminal amino group-containing polyorganosiloxane (4) synthesized in Synthesis Example 1, 730 parts by mass of a polydimethylsiloxane (2) (weight average molecular weight=approximately 3,000; in the general formula (2), n=approximately 38) of the following structure, 660 parts by mass of an amino-group-containing polyorganosiloxane (3) (weight average molecular weight=approximately 15,000) of the following structure, 1,700 parts by mass of toluene, and 200 parts by mass of ethanol were added, and the resulting admixture was stirred at 85° C. for two hours, to obtain a comparative coating agent 1.

[Chemical 12]

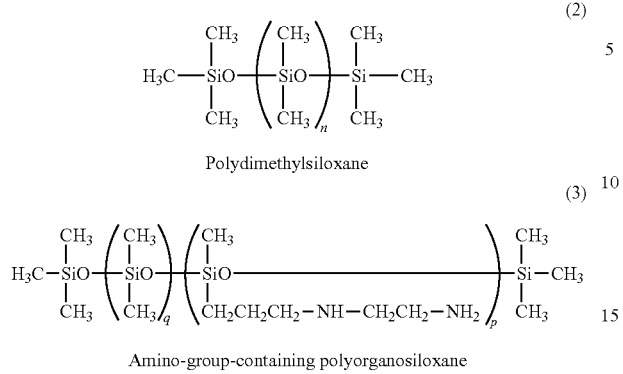

Polydimethylsiloxane (2)

Amino-group-containing polyorganosiloxane (3)

where p=5, p:q (molar ratio)=1:40

Examples 1 to 9 and Comparative Examples 2 and 3

A hydroxyl-group-containing polydimethylsiloxane (1) (weight average molecular weight=approximately 900,000) of the following structure, a polydimethylsiloxane (2)

[Chemical 13]

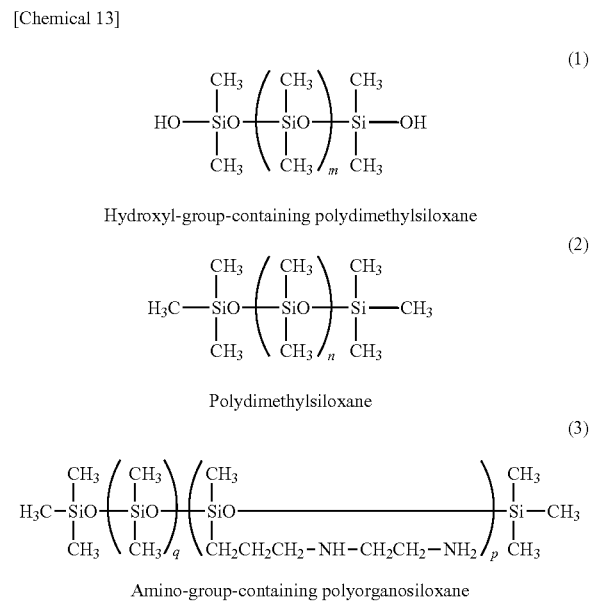

Hydroxyl-group-containing polydimethylsiloxane (1)

Polydimethylsiloxane (2)

Amino-group-containing polyorganosiloxane (3)

where p=5, p:q (molar ratio)=1:40

TABLE 1

|  |  | Com 2 | Ex 1 | Ex 2 | Ex 3 | Ex 4 | Ex 5 | Ex 6 | Ex 7 | Ex 8 | Ex 9 | Com 3 |
|---|---|---|---|---|---|---|---|---|---|---|---|---|
| Blending ratio (parts by mass) | Compound 1 | 100 | 100 | 100 | 100 | 100 | 100 | 100 | 100 | 100 | 100 | 100 |
|  | Compound 2 | 550 | 730 | 1,100 | 1,350 | 1,500 | 1,600 | 1,750 | 2,000 | 2,350 | 3,000 | 4,000 |
|  | Compound 3 | 990 | 990 | 990 | 990 | 990 | 990 | 990 | 990 | 990 | 990 | 990 |
|  | Total amount of Compounds 1-3 | 1,640 | 1,820 | 2,190 | 2,440 | 2,590 | 2,690 | 2,840 | 3,090 | 3,440 | 4,090 | 5,090 |
|  | Toluene | 1,200 | 1,200 | 1,200 | 1,200 | 1,200 | 1,200 | 1,200 | 1,200 | 1,200 | 1,600 | 2,000 |
|  | Ethanol | 100 | 100 | 100 | 100 | 100 | 100 | 100 | 100 | 100 | 100 | 100 |
|  | Total amount | 2,940 | 3,120 | 3,490 | 3,740 | 3,890 | 3,990 | 4,140 | 4,390 | 4,740 | 5,790 | 7,190 |
| Content (mass %) | Compound 1 | 6.1 | 5.5 | 4.6 | 4.1 | 3.9 | 3.7 | 3.5 | 3.2 | 2.9 | 2.4 | 2.0 |
|  | Compound 2 | 33.5 | 40.1 | 50.2 | 55.3 | 57.9 | 59.5 | 61.6 | 64.7 | 68.3 | 73.4 | 78.6 |
|  | Compound 3 | 60.4 | 54.4 | 45.2 | 40.6 | 38.2 | 36.8 | 34.9 | 32.0 | 28.8 | 24.2 | 19.4 |
| Mixing ratio (mass ratio) | Compound2/Compound 3 | 0.6 | 0.7 | 1.1 | 1.4 | 1.5 | 1.6 | 1.8 | 2.0 | 2.4 | 3.0 | 4.0 |

Compound 1: hydroxyl-group-containing polydimethylsiloxane (1)
Compound 2: polydimethylsiloxane (2)
Compound 3: amino-group-containing polyorganosiloxane (3)
Com: Comparative example
Ex: Example (weight average molecular weight=approximately 3,000; n in the general formula (2)=38) of the following structure, an amino-group-containing polyorganosiloxane (3) (weight average molecular weight=approximately 15,000) of the following structure, toluene and ethanol were added in such a manner as to obtain the compositions as set forth in Table 1 below, and each of the resulting admixtures was stirred and mixed at 85° C. for two hours, to obtain coating agents 1 to 9 (Examples 1 to 9) and comparative coating agents 2 and 3 (Comparative Examples 2 and 3). Note that in Table 1 below, the hydroxyl-group-containing polydimethylsiloxane (1) is referred to as "compound 1," the polydimethylsiloxane (2) is referred to as "compound 2," and the amino-group-containing polyorganosiloxane (3) is referred to as "compound 3."

For the coating agents 1 to 9 obtained in Examples 1 to 9 above and the comparative coating agents 1 to 3 obtained in Comparative Examples 1 to 3, piercing resistance was measured according to the following method.

[Measurement of Piercing Resistance]
(Injection Needle Coating 1: Heating)

Each coating agent was diluted by addition of dichloromethane in such a manner that the concentration of silicone components became approximately 5 mass %, to obtain a colorless transparent coating liquid. Note that the concentration of the silicone components, in Examples 1 to 9 and Comparative Examples 2 and 3, refers to the total concentration of the hydroxyl-group-containing polydimethylsiloxane (1), the polydimethylsiloxane (2) and the amino-group-containing polyorganosiloxane (3) in the coating liquid. For example, in Comparative Example 1, the concentration of the silicone components refers to the total concentration of the both terminal amino group-containing polyorganosiloxane (4), the polydimethylsiloxane (2) and the amino-group-containing polyorganosiloxane (3) in the coating liquid.

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was heated in an oven at 120° C. for two hours, to perform a curing treatment. Note that the injection needles formed on surfaces thereof with coating films using the coating agents 1 to 9 are referred to as injection needles 1 to 9, whereas the injection needles formed on surfaces thereof with coating films using the comparative coating agents 1 to 3 are referred to as comparative injection needles 1 to 3, respectively.

(Injection Needle Coating 2: EOG)

Coating liquids were prepared in the same manner as the aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was subjected to a curing treatment using ethylene oxide gas (EOG) at 50° C. for 210 minutes. Note that by the aforesaid treatment, the injection needle underwent EOG (ethylene oxide gas) sterilization. For example, the injection needles formed on surfaces thereof with coating films using the coating agents 1 to 9 are referred to as injection needles 10 to 18, whereas the injection needles formed on surfaces thereof with coating films using the comparative coating agents 1 to 3 are referred to as comparative injection needles 4 to 6, respectively.

(Injection Needle Coating 3: High-Pressure Steam)

Coating liquids were prepared in the same manner as in the aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was subjected to a curing treatment under a high-pressure steam at 121° C. for 20 minutes. Note that by the aforesaid treatment, the injection needle underwent high-pressure steam (autoclave) sterilization. For example, the injection needles formed on surfaces thereof with coating films using the coating agents 1 to 9 are referred to as injection needles 19 to 27, whereas the injection needles formed on surfaces thereof with coating films using the comparative coating agents 1 to 3 are referred to as comparative injection needles 7 to 9, respectively.

(Injection Needle Coating 4: Radiation)

Coating liquids were prepared in the same manner as the aforesaid (Injection Needle Coating 1: Heating).

In each of the coating liquids prepared as aforesaid, an 18G injection needle (with a needle part made of SUS304) was immersed, and the injection needle was pulled up at a rate of 1,000 mm/minute, by use of a tensile tester (Autograph AG-1kNIS, made by Shimadzu Corporation). Natural drying at room temperature was conducted for two hours. Further, the injection needle was subjected to a curing treatment by irradiating with γ rays at 20 kGy. Note that by the aforesaid treatment, the injection needle underwent radiation sterilization. For example, the injection needles formed on surfaces thereof with coating films using the coating agents 1 to 9 are referred to as injection needles 28 to 36, whereas the injection needles formed on surfaces thereof with coating films using the comparative coating agents 1 to 3 are referred to as comparative injection needles 10 to 12, respectively.

(Measurement of Piercing Resistance)

For the injection needles 1 to 36 and the comparative injection needles 1 to 12, sliding resistance value (piercing resistance value) (mN) at the time of puncturing a 50 μm-thick polyethylene film with the injection needle at an angle of 90 degrees and at a rate of 100 mm/minute was measured, using a tensile tester (Autograph AG-1kNIS, made by Shimadzu Corporation). Specifically, sliding resistance in relation to moving amount of the injection needle was obtained as time-series data. In addition, from the measurements, a maximum resistance value (mN) was calculated. Note that the measurement was conducted after the injection needles 1 to 36 and the comparative injection needles 1 to 12 were each made to puncture a rubber stopper zero time (initial stage) and ten times.

Figure 1B:
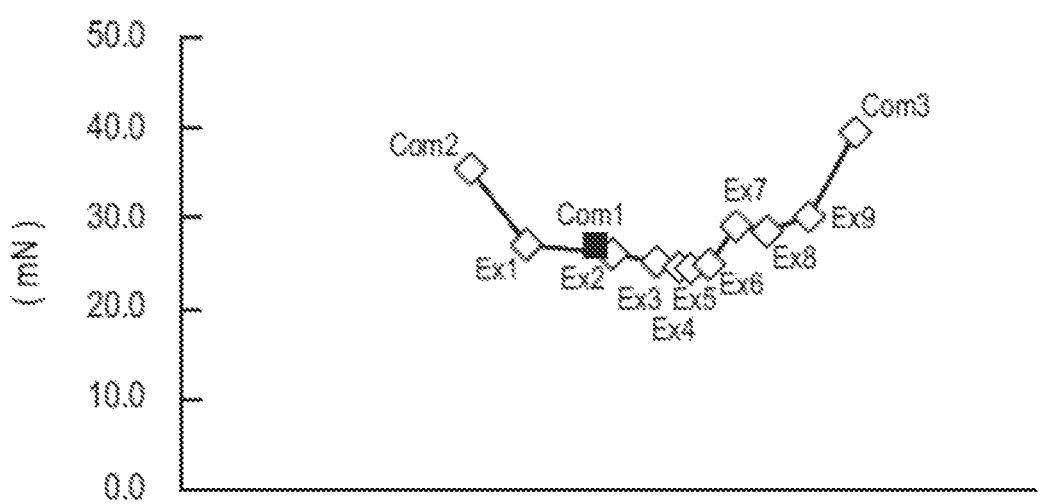
FIG. 1B is a graph depicting puncture resistance (sliding resistance value (mN)) at an initial stage (on puncturing zero time) of a needle surface treated with a coating agent by an EOG treatment, in Examples 1 to 9 (Ex. 1 to Ex. 9) and Comparative Examples 1 to 3 (Com. 1 to Com. 3).
Figure 1C:
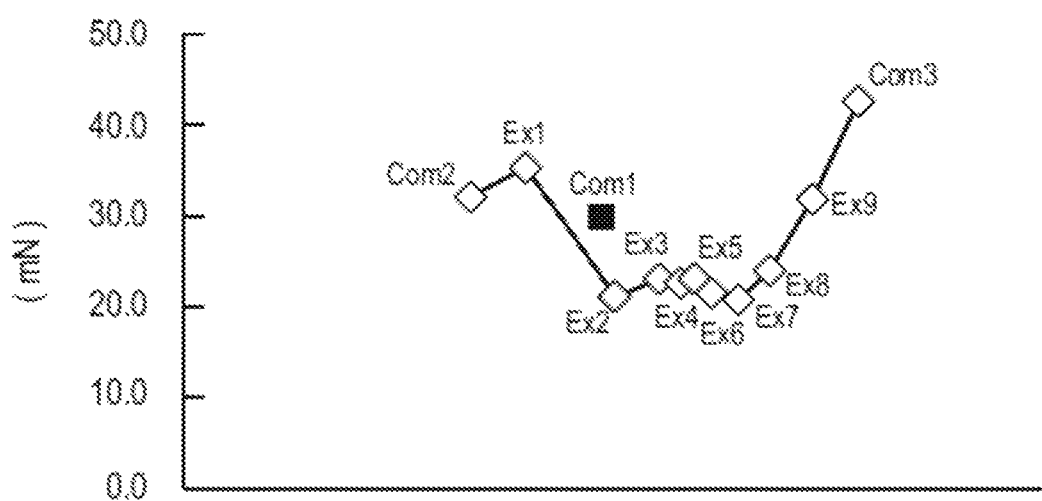
FIG. 1C is a graph depicting puncture resistance (sliding resistance value (mN)) at an initial stage (on puncturing zero time) of a needle surface treated with a coating agent by a high-pressure steam treatment, in Examples 1 to 9 (Ex. 1 to Ex. 9) and Comparative Examples 1 to 3 (Com. 1 to Com. 3).
Figure 2A:
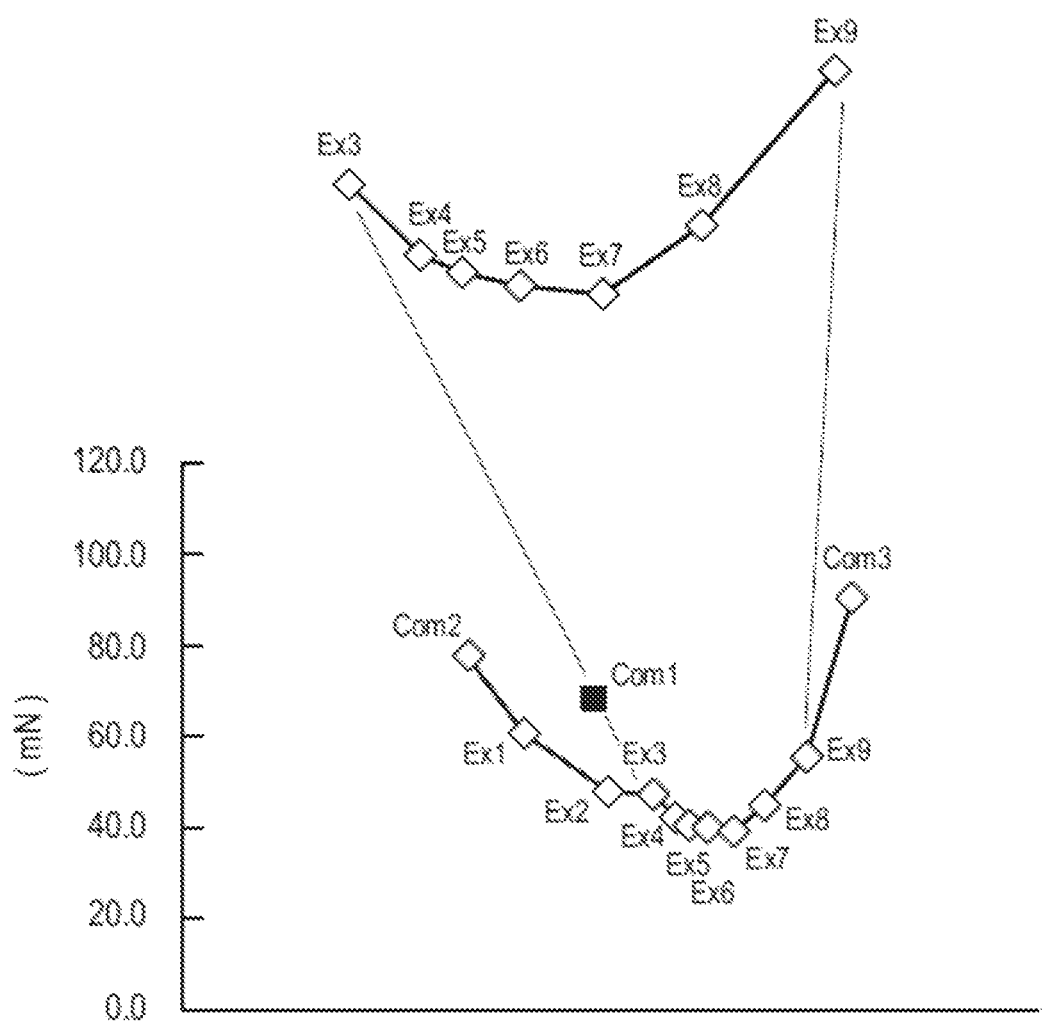
FIG. 2A is a graph depicting puncture resistance (sliding resistance value (mN)), on puncturing ten times, of a needle surface treated with a coating agent by heating, in Examples 1 to 9 (Ex. 1 to Ex. 9) and Comparative Examples 1 to 3 (Com. 1 to Com. 3). Note that in FIG. 2A, a partially enlarged graph is jointly depicted for easier comparison of Examples 3 to 9 (Ex. 3 to Ex. 9).
Figure 2B:
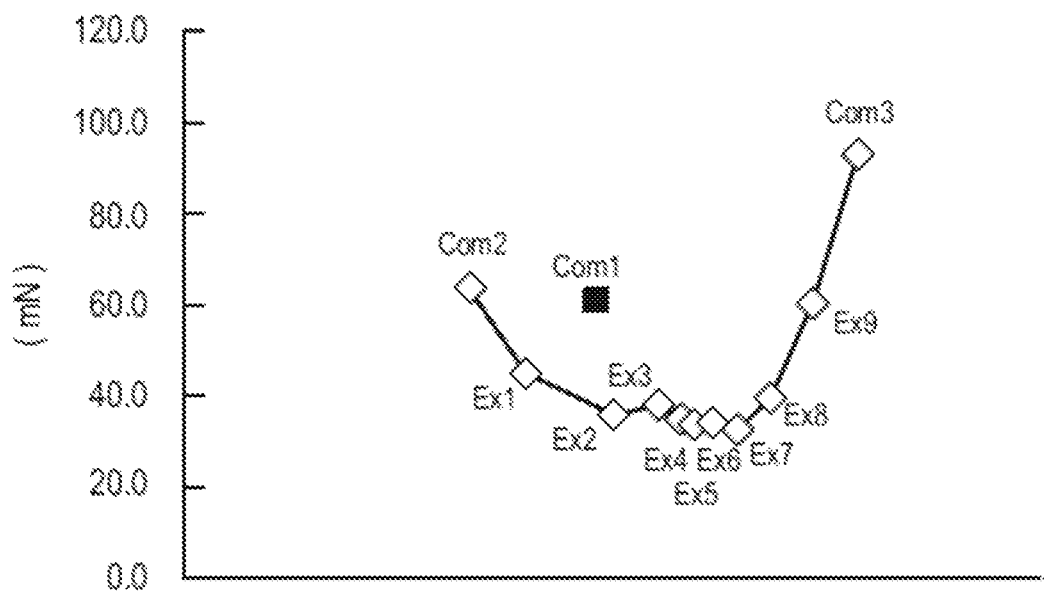
FIG. 2B is a graph depicting puncture resistance (sliding resistance value (mN)), on puncturing ten times, of a needle surface treated with a coating agent by an EOG treatment, in Examples 1 to 9 (Ex. 1 to Ex. 9) and Comparative Examples 1 to 3 (Com. 1 to Com. 3).
Figure 2C:
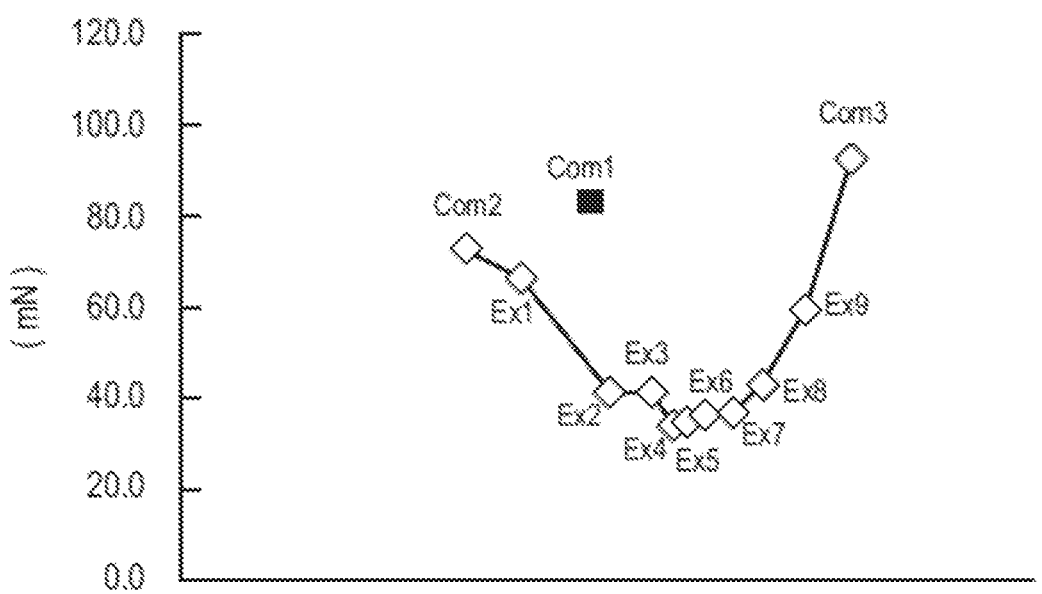
FIG. 2C is a graph depicting puncture resistance (sliding resistance value (mN)), on puncturing ten times, of a needle surface treated with a coating agent by a high-pressure steam treatment, in Examples 1 to 9 (Ex. 1 to Ex. 9) and Comparative Examples 1 to 3 (Com. 1 to Com. 3).

The results are depicted in FIGS. 1 and 2. In detail, the results of sliding resistance value (piercing resistance value) (mN) upon puncturing zero time and upon puncturing ten times, for the injection needles 1 to 9 and the comparative injection needles 1 to 3 (coating 1: heating at 105° C. for 24 hours), are depicted in FIG. 1A and FIG. 2A, respectively. Note that in FIG. 2A, an enlarged view obtained by extracting only the results of the sliding resistance value (piercing resistance value) (mN) upon puncturing ten times, for the injection needles 3 to 9 (coating 1: heating at 105° C. for 24 hours) is jointly depicted. In addition, the results of sliding resistance value (piercing resistance value) (mN) upon puncturing zero time and upon puncturing ten times, for the injection needles 10 to 18 and the comparative injection needles 4 to 6 (coating 2: EOG treatment), are depicted in FIG. 1B and FIG. 2B, respectively. For example, the results of sliding resistance value (piercing resistance value) (mN) upon puncturing zero time and upon puncturing ten times, for the injection needles 19 to 27 and the comparative injection needles 7 to 9 (coating 3: high-pressure steam treatment), are depicted in FIG. 1C and FIG. 2C, respectively. Note that in FIGS. 1 and 2, the axis of ordinates represents sliding resistance value (unit: mN). For example, the axis of abscissas represents Examples and Comparative Examples. Note that the plots in the polygonal lines in FIGS. 1 and 2 represent Comparative Example 2 (Com. 2), Example 1 (Ex. 1), Example 2 (Ex. 2), Example 3 (Ex. 3), Example 4 (Ex. 4), Example 5 (Ex. 5), Example 6 (Ex. 6), Example 7 (Ex. 7), Example 8 (Ex. 8), Example 9 (Ex. 9) and Comparative Example 3 (Com. 3), from the left. "Com. 1" in FIGS. 1 and 2 represents Comparative Example 1.

From FIGS. 1 and 2, the injection needles according to an exemplary aspect exhibited sliding resistance values (piercing resistance values) comparable to or not more than those of the comparative injection needles upon puncturing zero time, but exhibited sliding resistance values (piercing resistance values) significantly lower than those of the comparative injection needles upon puncturing ten times. Therefore, it is considered that according to the injection needles according to an exemplary aspect, durability can be enhanced. In addition, from the enlarged view in FIG. 2A, it is considered that the injection needles (injection needles 4 to 7) formed on surfaces thereof with coating films by using the coating agents 4 to 7 can exhibit particularly remarkably a friction (puncture resistance)-reducing effect and a durability-enhancing effect at the time of puncturing. The same or similar effects to the aforesaid are observed also for the other injection needles (injection needles 13 to 16, and 22 to 25) formed on surfaces thereof with coating films by using the coating agents 4 to 7.

Note that while the results in regard of coating 4 (γ ray irradiation) are not illustrated, sliding resistance values (piercing resistance values) (mN) after puncturing a rubber stopper with the injection needles 28 to 36 zero time were significantly lower than those with the comparative injection needles 11 and 12, and were substantially the same as that with the comparative injection needle 10. In addition, sliding resistance values (piercing resistance values) (mN) after puncturing a rubber stopper with the injection needles 29 to 35 ten times exhibited sliding resistance values (piercing resistance values) significantly lower than those with the comparative injection needles 10 to 12. Further, the injection needles 31 to 34 formed on surfaces thereof with coating films by using the coating agents 4 to 7 were particularly remarkable in a friction (puncture resistance)-reducing effect and a durability-enhancing effect at the time of puncturing, and gave the same or similar effects to the aforesaid.

Therefore, it is considered that according to the injection needle according to an exemplary aspect, durability and piercing characteristics can be enhanced. In addition, by the aforesaid effects, it is expected that the coating agent according to an exemplary aspect can exhibit the same or similar lubricating property and durability to the aforesaid, also when applied to other medical instruments than needles.

What is claimed is:

1. A coating agent comprising:
   (a) a hydroxyl-group-containing polyorganosiloxane represented by the following general formula (1):

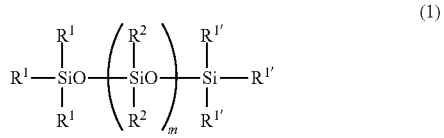

(1)

wherein each $R^1$ and each $R^{1'}$ independently represents a monovalent hydrocarbon group or a hydroxyl group (—OH), provided that at least one of $R^1$ and at least one of $R^{1'}$ is the hydroxyl group (—OH),
   each $R^2$ independently represents a monovalent hydrocarbon group, and
   m is an integer of 1,000 to 30,000;
   (b) a polydiorganosiloxane represented by the following general formula (2):

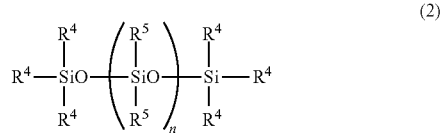

(2)

wherein each $R^4$ and each $R^5$ independently represents a monovalent hydrocarbon group, and
   n is an integer of 8 to 1,000; and (c) an amino-group-containing polyorganosiloxane containing at least one amino group in one molecule thereof represented by the following general formula (3):

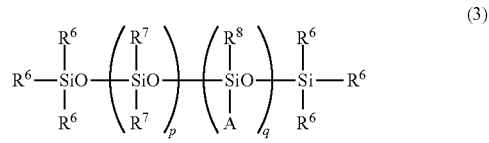

(3)

where each $R^6$ independently represents a monovalent hydrocarbon group or a —$OR^9$ group, wherein each $R^9$ independently represents a substituted or unsubstituted $C_1$-$C_4$ monovalent hydrocarbon group,
   each $R^7$ and each $R^8$ independently represents a monovalent hydrocarbon group,
   each A independently represents an amino-group-containing group,
   a ratio of p:q is in a range of from 5:1 to 100:1, and
   q is an integer of 1 to 100,
   wherein the polydiorganosiloxane (b) is contained in a proportion of a mass ratio to the amino-group-containing polyorganosiloxane (c) of from 0.7:1 to 3.0:1, and
   the hydroxyl-group-containing polyorganosiloxane (a) is contained in a proportion of 2.4 to 5.5 mass %, based on the total mass of the hydroxyl-group-containing polyorganosiloxane (a), the polydiorganosiloxane (b), and the amino-group-containing polyorganosiloxane (c).

2. The coating agent according to claim 1, wherein the polydiorganosiloxane (b) is contained in a proportion of 40 to 75 mass %, based on the total mass of the hydroxyl-group-containing polyorganosiloxane (a), the polydiorganosiloxane (b), and the amino-group-containing polyorganosiloxane (c).

3. The coating agent according to claim 1, wherein in the general formula (1), one of $R^1$ is a hydroxyl group, one of $R^{1'}$ is a hydroxyl group, and each of the remaining $R^1$ and $R^{1'}$ independently is a $C_1$-$C_4$ straight-chain or branched alkyl group, and each $R^2$ is independently a $C_1$-$C_4$ straight-chain or branched alkyl group.

4. The coating agent according to claim 1, wherein in the general formula (2), $R^4$ and $R^5$ are each independently a $C_1$-$C_4$ straight-chain or branched alkyl group.

5. The coating agent according to claim 1, wherein in the general formula (3), $R^6$ is each independently a $C^1$-$C^4$ straight-chain or branched alkyl group, $R^7$ and $R^8$ are each independently a $C_1$-$C_4$ straight-chain or branched alkyl group, and A is γ-aminopropyl group, N-(β-aminoethyl)aminomethyl group or γ-(N-(β-aminoethyl)amino)propyl group.

6. The coating agent according to claim 1, wherein in the general formula (1), one of $R^1$ is a hydroxyl group, one of $R^{1'}$ is a hydroxyl group, each of the remaining $R^1$ and $R^{1'}$ groups is a methyl group, and $R^2$ is a methyl group.

7. The coating agent according to claim 1, wherein in the general formula (2), $R^4$ and $R^5$ are each independently a $C_1$-$C_4$ straight-chain or branched alkyl group.

8. The coating agent according to claim 1, wherein in the general formula (2), $R^4$ is a methyl group and $R^5$ is a methyl group.

9. The coating agent according to claim 1, wherein in the general formula (3), $R^6$ is each independently a $C_1$-$C_4$ straight-chain or branched alkyl group, $R^7$ and $R^8$ are each independently a $C_1$-$C_4$ straight-chain or branched alkyl group, and A is γ-aminopropyl, N-(β-aminoethyl)aminomethyl or γ-(N-(β-aminoethyl)amino)propyl group.

10. The coating agent according to claim 1, wherein in the general formula (3), $R^6$ is a methyl group, $R^7$ is a methyl group, $R^8$ is a methyl group, and A is γ-(N-(β-aminoethyl)amino)propyl.

11. A method for surface treating a medical instrument, the method comprising:
   forming a coating film on a surface of a medical instrument, wherein the coating film comprises the coating agent according to claim 1, an
   curing the coating film.

12. The method according to claim 11, wherein the step of curing the coating film comprises heating the coating film at a temperature of from 50° C. to 150° C. for a duration of from 2 to 48 hours.

13. The method according to claim 11, wherein the step of curing the coating film comprises heating the coating film under compressed steam at a temperature of from 100° C. to 135° C. for a duration of from 1 to 120 minutes.

14. The method according to claim 11, wherein the step of curing the coating film comprises heating the coating film using ethylene oxide gas at a temperature of from 40° C. to 135° C. for a duration of from 1 to 300 minutes.

15. The method according to claim 11, wherein the step of curing the coating film comprises irradiating the coating film with radiation, wherein the radiation comprises gamma rays, electron beams, neutron beams, or X rays.

16. The method according to claim 11, wherein the medical instrument is a needle.

17. A medical instrument obtained from the method according to claim 11.

18. A puncture needle coated with a coating agent on a peripheral surface of a tip portion of a puncture portion thereof, the coating agent including:
   (a) a hydroxyl-group-containing polyorganosiloxane represented by the following general formula (1):

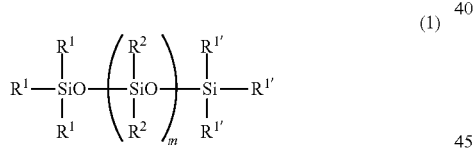

(1)

where each $R^1$ and each $R^{1'}$ independently represents a monovalent hydrocarbon group or a hydroxyl group (—OH), provided that at least one of $R^1$ and at least one of $R^{1'}$ is the hydroxyl group (—OH),
each $R^2$ independently represents a monovalent hydrocarbon group, and
m is an integer of 1,000 to 30,000;
(b) a polydiorganosiloxane represented by the following general formula (2):

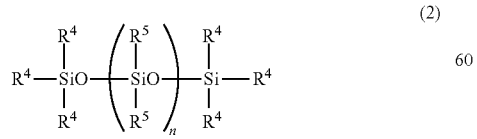

(2)

wherein each $R^4$ and $R^5$ independently represents a monovalent hydrocarbon group, and
n is an integer of 8 to 1,000; and (c) an amino-group-containing polyorganosiloxane containing at least one amino group in one molecule thereof represented by the following general formula (3):

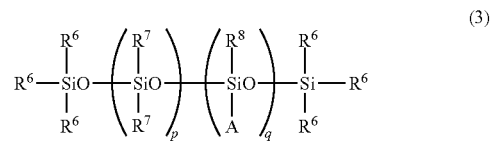

(3)

wherein each $R^6$ independently represents a monovalent hydrocarbon group or a —$OR^9$ group, wherein each $R^9$ independently represents a substituted or unsubstituted $C_1$-$C_4$ monovalent hydrocarbon group,
each $R^7$ and each $R^8$ independently represents a monovalent hydrocarbon group,
each A independently represents an amino-group-containing group,
a ratio of p:q is in a range of from 5:1 to 100:1, and
q is an integer of 1 to 100,
wherein the polydiorganosiloxane (b) is contained in a proportion of a mass ratio to the amino-group-containing polyorganosiloxane (c) of from 0.7:1 to 3.0:1, and
the hydroxyl-group-containing polyorganosiloxane (a) is contained in a proportion of 2.4 to 5.5 mass %, based on the total mass of the hydroxyl-group-containing polyorganosiloxane (a), the polydiorganosiloxane (b), and the amino-group-containing polyorganosiloxane (c).

19. A method of producing a puncture needle coated with a coating agent, the method comprising:
   a step of coating the puncture needle with a coating agent; and
   a step of subjecting the coating agent to a curing treatment by heating or irradiating with radiation, the coating agent including:
   (a) a hydroxyl-group-containing polyorganosiloxane represented by the following general formula (1):

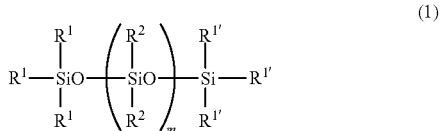

(1)

wherein each $R^1$ and each $R^{1'}$ independently represents a monovalent hydrocarbon group or a hydroxyl group (—OH), provided that at least one of $R^1$ and at least one of $R^{1'}$ is the hydroxyl group (—OH),
each $R^2$ independently represents a monovalent hydrocarbon group, and
m is an integer of 1,000 to 30,000;
(b) a polydiorganosiloxane represented by the following general formula (2):

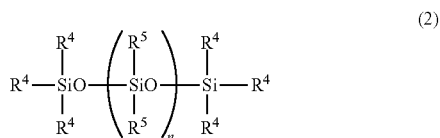

(2)

wherein each $R^4$ and $R^5$ each independently represent a monovalent hydrocarbon group, and n is an integer of 8 to 1,000; and (c) an amino-group-containing polyorganosiloxane containing at least one amino group in one molecule thereof represented by the following general formula (3):

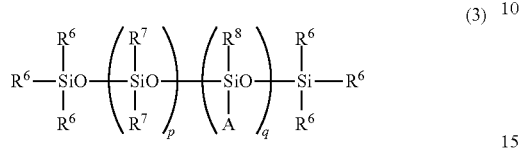
(3)

where $R^6$ each independently represents a monovalent hydrocarbon group or a —$OR^9$ group, wherein each $R^9$ independently represents a substituted or unsubstituted $C_1$-$C_4$ monovalent hydrocarbon group, each $R^7$ and each $R^8$ independently represents a monovalent hydrocarbon group, each A independently represents an amino-group-containing group, a ratio of p:q is in a range of from 5:1 to 100:1, and q is an integer of 1 to 100, wherein the polydiorganosiloxane (b) is contained in a proportion of a mass ratio to the amino-group-containing polyorganosiloxane (c) of from 0.7:1 to 3.0:1, and the hydroxyl-group-containing polyorganosiloxane (a) is contained in a proportion of 2.4 to 5.5 mass %, based on the total mass of the hydroxyl-group-containing polyorganosiloxane (a), the polydiorganosiloxane (b), and the amino-group-containing polyorganosiloxane (c).

* * * * *